US012661473B2

(12) United States Patent
Hansmann et al.

(10) Patent No.: US 12,661,473 B2
(45) Date of Patent: Jun. 23, 2026

(54) DEVICE AND PROCESS FOR CONNECTING A PATIENT-SIDE COUPLING UNIT TO A SOURCE OR TO A SINK FOR A GAS

(71) Applicant: Drägerwerk AG & Co. KGaA, Lübeck (DE)

(72) Inventors: Hans-Ullrich Hansmann, Lübeck (DE); Sebastian Schröter, Lübeck (DE); Jöran Blendermann, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 714 days.

(21) Appl. No.: 18/150,263

(22) Filed: Jan. 5, 2023

(65) Prior Publication Data

US 2023/0211108 A1     Jul. 6, 2023

(30) Foreign Application Priority Data

Jan. 6, 2022    (DE) .................... 10 2022 100 254.3

(51) Int. Cl.
| | |
|---|---|
| *A61M 16/08* | (2006.01) |
| *A61M 16/00* | (2006.01) |
| *A61M 16/20* | (2006.01) |

(52) U.S. Cl.
CPC ...... *A61M 16/0816* (2013.01); *A61M 16/202* (2014.02); *A61M 16/204* (2014.02); *A61M 2016/0033* (2013.01)

(58) Field of Classification Search
CPC .. A61M 16/20; A61M 16/201; A61M 16/202; A61M 16/203; A61M 16/204; A61M 16/205; A61M 16/12
See application file for complete search history.

(56) References Cited

U.S. PATENT DOCUMENTS

| | | | |
|---|---|---|---|
| 2009/0126734 A1 * | 5/2009 | Dunsmore | ........ A61M 16/0858 |
| | | | 128/204.23 |
| 2020/0316327 A1 * | 10/2020 | Hansmann | .......... A61M 16/205 |

FOREIGN PATENT DOCUMENTS

| | | | | |
|---|---|---|---|---|
| EP | 0056148 A1 * | 7/1982 | ............ | A61M 16/00 |
| WO | WO-2021188909 A1 * | 9/2021 | .......... | A61M 16/202 |

* cited by examiner

*Primary Examiner* — Joseph D. Boecker
*Assistant Examiner* — Jaeick Jang
(74) *Attorney, Agent, or Firm* — McGlew and Tuttle, P.C.

(57) ABSTRACT

A connection device and process connect a patient-side coupling unit to a source/sink of a gas including oxygen. The connection device includes a valve device with a first valve (40.1) and with a second valve (40.2). A source-side fluid guide unit establishes a fluid connection between the source or the sink and the valve device. A patient-side fluid guide unit establishes a fluid connection between the patient-side coupling unit and the valve device. The valves are connected in parallel and are arranged between the two fluid guide units. A gas flows from the source through the first and/or second valve to the patient-side coupling unit or through the first and/or second valves to the sink. A control pressure is set at each valve. As a result, the time course of the volume flow downstream of the valve device follows a predefined time course.

13 Claims, 7 Drawing Sheets

DEVICE AND PROCESS FOR CONNECTING A PATIENT-SIDE COUPLING UNIT TO A SOURCE OR TO A SINK FOR A GAS

CROSS REFERENCE TO RELATED APPLICATIONS

This application claims the benefit of priority under 35 U.S.C. § 119 of German Application 10 2022 100 254.3, filed Jan. 6, 2022, the entire contents of which are incorporated herein by reference.

TECHNICAL FIELD

The present invention pertains to a device and to a process for connecting a patient-side coupling unit to a source and/or to a sink for a gas. The gas comprises oxygen. The patient-side coupling unit is at least temporarily connected or can be connected to a patient.

The device according to the present invention and the process according to the present invention can be used to ventilate the patient artificially. The patient-side coupling unit is arranged in or at or on the body of the patient. The gas flows from at least one source through an inhalation duct to the patient-side coupling unit. Exhaled gas flows away from the patient-side coupling unit through an exhalation duct.

BACKGROUND

It is desired to control by closed-loop control or at least by open-loop control the volume flow through the inhalation duct and/or through the exhalation duct to or from the patient-side coupling unit and/or the pressure in the inhalation duct and/or in the exhalation duct. The control gain of the control is to have the actual time course of the volume flow and/or the pressure to follow a predefined desired time course. The present invention is used in this application in the inhalation duct and/or in the exhalation duct.

SUMMARY

A basic object of the present invention is to provide a connection device and a process for connecting a patient-side coupling unit to a source and/or to a sink for a gas, wherein the gas flows from the source through an inhalation duct to the patient-side coupling unit and/or through an exhalation duct away from the patient-side coupling unit to the sink and wherein the actual time course of a volume flow or of a pressure can be better controlled than in prior-art connection devices and processes.

The present invention is accomplished by a connection device having features according to the invention and by a connection process having features according to the invention. Advantageous embodiments are described herein. Advantageous embodiments of the connection device are, insofar as meaningful, also advantageous embodiments of the connection process according to the present invention and vice versa.

The connection device according to the present invention is capable of connecting a patient-side coupling unit to a source or to a sink for a gas. This gas preferably comprises oxygen and/or air. The gas optionally comprises, in addition, at least one anesthetic agent (anesthetic). The gas may also be air exhaled by the patient and may additionally comprise carbon dioxide. An embodiment of the connection device according to the present invention is optionally capable of connecting the patient-side coupling unit both to the source and to the sink. It is possible that the same medical device acts both as a source and as a sink. The gas can also be a component of a gas mixture wherein the gas mixture is conveyed to the patient-side coupling unit or is discharged away from the patient-side coupling unit. The source is a supplying connector for supplying the gas component. Or the source is a medical device or the patient-side coupling unit, e.g. The source can also be a mixing point in which the gas mixture is created or develops. The sink is a stationary or mobile receptacle for a gas, in particular for a gas comprising an anesthetic. In the case of a breathing circuit the sink may be the medical device.

The patient-side coupling unit is at least temporarily connected or can be connected to a patient. In particular, the patient-side coupling unit is arranged in or at or on the body of the patient.

The connection device according to the present invention comprises a valve device and two fluid guide units, namely a source-side fluid guide unit and a patient-side fluid guide unit. A "fluid guide unit" is defined as a component that is capable of guiding a fluid along a trajectory and ideally completely prevents the fluid from leaving this trajectory. A rigid tube and a flexible hose are two examples of a fluid guide unit. The fluid guide unit may be a two-lumen hose.

The source-side fluid guide unit establishes at least temporarily a fluid connection between the source or the sink for the gas and the valve device or is capable of establishing such a fluid connection. The patient-side fluid guide unit establishes at least temporarily a fluid connection between the patient-side coupling unit and the valve device or is capable of establishing such a fluid connection. The two fluid guide units are preferably connected in series via the valve device.

The gas flows in a flow direction from the source to the patient-side coupling unit or from the patient-side coupling unit to the sink. The terms "upstream" and "downstream" are related to this flow direction. The one fluid guide unit is arranged upstream, and the other fluid guide unit is arranged downstream of the valve device. Whether the source-side fluid guide unit or the patient-side fluid guide unit is the fluid guide unit arranged upstream depends on the flow direction and hence on the use of the present invention.

The connection device according to the present invention comprises, furthermore, the valve device. This valve device comprises a first valve and at least one second valve, and optionally a plurality of second valves (one or more additional valves). A "valve" is defined as a component through which a fluid can flow, wherein the component is capable of changing and, as a rule, especially completely preventing the volume flow of the fluid through the valve within a construction-related range. The valve may change the volume flow in increments or continuously. The "volume flow" is an indicator of the volume per unit of time of the fluid, which flows through the valve or through a fluid guide unit.

The second valve or at least one second valve of the valve device is connected in parallel to the first valve. During the flow from the fluid guide unit arranged upstream to the fluid guide unit arranged downstream, the gas flows through at least one valve of the valve device, i.e., through the first valve and/or through the second valve and/or through at least one second valve. It is possible that the gas flows only through one valve at a given time because the other valve is closed. It is also possible that the gas flows at a given time simultaneously through both valves or through at least two valves connected in parallel.

A signal-processing control unit of the connection device according to the present invention is capable of automatically setting a respective control pressure at each valve of the valve device. The control pressures at the valves may differ from one another. The setting of the control pressure at a valve causes the volume flow through this valve to be set at a defined value. In addition, the setting of the control pressure affects the pressure in the fluid guide unit arranged downstream.

Due to the control unit setting a respective control pressure automatically at each valve of the valve device, the control unit is capable of automatically controlling the volume flow through and/or the pressure in the fluid guide unit arranged downstream. The control gain of the setting of the control pressure is to have the time course of the actual volume flow through the fluid guide unit arranged downstream or the pressure in this fluid guide unit to follow a predefined time course.

The connection process according to the present invention is carried out automatically with the use of a connection device according to the present invention. The gas flows from the source to the patient-side coupling unit or from the patient-side coupling unit to the sink. The volume flow through the fluid guide unit arranged downstream or the pressure in the fluid guide unit arranged downstream is controlled by closed-loop control or open-loop control. As a result, the time course of the actual volume flow or or of the pressure follows a predefined time course. The step of controlling the volume flow or the pressure comprises the step of setting and optionally changing a respective control pressure at least once at the first valve and/or at the second valve or at the at least one second valve. It is also possible that both the volume flow and the pressure are controlled.

The inventors determined in internal experiments that the volume flow or the pressure can be controlled more easily when the gas can flow through two valves connected in parallel, compared to an embodiment in which the gas only flows through one valve. The present invention makes it possible to control the volume flow or the pressure in the fluid guide unit arranged downstream relatively reliably, even if the volume flow and/or the pressure in the fluid guide unit arranged upstream is subject to great variations over time or may at least vary greatly.

In many cases, the present invention eliminates the need to switch the valve device over abruptly from one state to another state. Rather, it is possible to continuously or smoothly reduce the volume flow through the one valve of the valve device and also to continuously or smoothly increase the volume flow through the other valve in an overlapping manner over time. As a result, the risk of an oscillation of the volume flow and/or of the pressure in an undesired extent is reduced thereby.

At least two valves of the valve device according to the present invention are connected in parallel and both are arranged between the two fluid guide units.

In one application, the connection device according to the present invention connects the patient-side coupling unit to a source for the gas. The source is, for example, a stationary supply port for the gas or it comprises at least one cylinder or other receptacle containing the gas or a fluid guide unit for the gas. It is also possible that the source is a mixing point, at which the gas being a gas mixture is obtained by mixing the gas from at least two gas components. The source may also be a ventilator, which carries out a sequence of ventilation strokes and feeds a respective quantity of a gas into the source-side fluid guide unit during each ventilation stroke. The present invention is used in these applications in an inhalation (inspiration) duct, which leads from the source to the patient-side coupling unit and in which the gas is delivered to the patient-side coupling unit. The connection device is arranged in the inhalation duct in this application. The source-side fluid guide unit is the fluid guide unit arranged upstream and the patient-side fluid guide unit is the fluid guide unit arranged downstream.

In another application, the connection device according to the present invention connects the patient-side coupling unit to a sink for the gas. The sink is, for example, the surrounding area or a stationary fluid receptacle. The source-side fluid guide unit is the fluid guide unit arranged downstream, and the patient-side fluid guide unit is the fluid guide unit arranged upstream.

It is also possible that a closed circuit, for example, a closed ventilation circuit for the artificial ventilation of a patient, is established between the patient-side coupling unit and a medical device. The medical device, e.g. an anesthesia apparatus, acts both as a source and as a sink in this embodiment. A fluid conveying unit maintains a flow of gas in the ventilation circuit. The sink is, for example, the fluid conveying unit in this application, and the gas flows from the patient-side coupling unit to this sink, i.e., to the fluid conveying unit. The present invention is used in these applications in an exhalation (expiration) duct, which leads from the patient-side coupling unit to the sink and to which the connection device belongs.

It is also possible to use the present invention both in an inhalation duct and in an exhalation duct, i.e., twice. An example of such a dual application is a ventilation circuit, in which a fluid conveying unit maintains a flow of gas, wherein a gas is delivered through the inhalation duct to the patient-side coupling unit and exhaled gas flows from the patient-side coupling unit through the exhalation duct.

According to a preferred embodiment, a respective pre-pressure (admission pressure) is present at each valve of the valve device. The pre-pressure present at the valve depends on the pressure in the fluid guide unit arranged upstream. It is especially preferred that the pre-pressure that is present at the valve is equal to the pressure in the fluid guide unit arranged upstream. The volume flow through the fluid guide unit arranged downstream depends on both the pre-pressure that is present at the valve and on the control pressure that is set at the valve by the control unit.

In a preferred embodiment, each valve of the valve device comprises a respective valve body and a valve body seat. On its way from the fluid guide unit arranged upstream to the fluid guide unit arranged downstream, the gas is capable of flowing through the valve body seat. Each valve body seat has a respective construction-related cross-sectional area. The valve body can move relative to the valve body seat. The position of the valve body relative to the valve body seat determines the effective cross-sectional area that is available for the gas for flowing through this valve. The effective cross-sectional area is smaller than or equal to the construction-related maximal cross-sectional area.

Preferably the control pressure present at the valve acts on the valve body and aims to press the valve body against the valve body seat. The control pressure therefore determines the force with which the valve body is pressed against the valve body seat. Preferably the pre-pressure aims at moving the valve body away from the valve body seat.

According to an implementation of this preferred embodiment, the construction-related cross-sectional area of one valve body seat is smaller than the cross-sectional area of the other or at least one other valve body seat. It is, however, also possible that both or at least two valve body seats have the same construction-related cross-sectional area, and all valve body seats optionally have the same construction-related cross-sectional area. Preferably, the control unit of the connection device according to the present invention causes the gas to flow exclusively through the valve with the smaller cross-sectional area in case of a volume flow below a first threshold and to flow exclusively through the valve with the larger cross-sectional area in case of a volume flow above a second threshold, wherein the second threshold is higher than the first threshold or is equal to the first threshold.

In one embodiment, a controllable fluid conveying unit is associated with at least one valve of the valve device. This fluid conveying unit is or comprises especially a pump or a blower or a piston-cylinder unit. It is possible that a separate respective fluid controllable fluid conveying unit is associated with each valve. It is also possible that the same controllable fluid conveying unit is associated with two different valves of the valve device.

The fluid conveying unit or each fluid conveying unit is capable of setting and changing the control pressure, which is present at the associated valve or at each associated valve. The signal-processing control unit (control device) of the connection device is capable of controlling the fluid conveying unit with the subordinate control gain that the fluid conveying unit sets the control pressure at the associated valve. The control pressure set—more precisely, a desired value for the control pressure to be set—depends on the measured volume flow to the valves connected in parallel. The control unit receives measured values from a sensor, which measures an indicator of the volume flow upstream of the valve device, and it calculates the desired value for the control pressure to be set by the fluid conveying unit.

This embodiment makes it possible to compensate for the inevitable influence of the volume flow on the back pressure, i.e., on the pressure downstream of the valve, to a certain degree.

Each valve of the valve device preferably has three coupling points, namely, a pre-pressure-side coupling point, a back pressure-side coupling point, and a control pressure-side coupling point. The pre-pressure-side coupling point is in a fluid connection with the fluid guide unit arranged upstream. Thus, a pre-pressure is present at the pre-pressure-side coupling point. The back pressure-side coupling point is in a fluid connection with the fluid guide unit arranged downstream. A back pressure is thus generated or occurs at the back pressure-side coupling point. The control pressure, which can be set and changed, is present at the control pressure-side coupling point.

In an implementation of this embodiment, the pre-pressure-side coupling point of a first valve is in a fluid connection with the control pressure-side coupling point of a second valve of the valve device. Thanks to this embodiment, the pre-pressure, which is present at this first valve, acts at the same time as a control pressure for the second valve. This implementation therefore eliminates the need for a fluid conveying unit for the second valve.

According to the present invention, the valve device comprises a first valve and at least one second valve. In one embodiment, the valve device comprises a second valve and additionally a third valve. The three valves are connected in parallel. All three valves are arranged between the source-side fluid guide unit and the patient-side fluid guide unit.

In one implementation of this embodiment, the pre-pressure-side coupling point of the second valve is in a fluid connection with the control pressure-side coupling point of the third valve. The pre-pressure at the second valve therefore acts as a control pressure for the third valve.

In one embodiment, a controllable fluid conveying unit, especially a pump or a blower, is associated with the first valve. This fluid conveying unit is capable of setting the control pressure, which is present at the first valve. The control pressure, which is present at the second valve, becomes established depending on the pre-pressure, which is present at the second valve, and on the control pressure, which is present at the first valve. This embodiment eliminates in many cases the need for a further fluid conveying unit for the second valve or for the optional third valve.

The invention further relates to a connection arrangement comprising a connection device according to the invention and a fluid conveying (delivery) device. The connection arrangement is capable of supplying a patient-side coupling unit with a gas. The fluid conveying device is capable of conveying (delivering) the gas through the connection arrangement to the patient-side coupling unit. The gas flows from a source first through the source-side fluid guide unit, afterwards through the valve device, and afterwards through the fluid conveying device to the patient side coupling unit. The source is a medical device or supply connection or supply port, e.g.

As a rule, the gas comprises oxygen. In one embodiment the gas has the form of a gas mixture, and the gas mixture additionally comprises at least one further component, e.g. breathing air and/or at least one anesthetic. This gas mixture is created in a mixing point or develops in the mixing point wherein at least two gas components are mixed in the mixing point. This mixing point serves as the source for the gas (the gas mixture).

The invention further refers to a discharge arrangement comprising a connection device according to the invention. The gas flows from the patient-side coupling unit through the patient-side fluid guide unit, afterwards through the valve device, and afterwards through the source-side fluid guide unit to a sink for the gas. This sink can be a fluid receptacle (fluid receiving unit) or a medical device. In particular the gas is breathed air (exhaled air) which a patient exhales wherein the patient is connected with the patient-side coupling unit.

In addition, the invention relates to a fluid circuit arrangement. This fluid circuit arrangement is capable of at least temporarily establishing and keeping a fluid circuit between a medical device and a patient-side coupling unit. In particular, the medical device is a ventilator, especially an anesthetic machine. The fluid circuit arrangement comprises a connection device according to the embodiment wherein the connection device connects the medical device with the patient-side coupling unit. The connection device comprises two source-side fluid guide units, namely a source-side inspiration fluid guide unit and a source-side expiration fluid guide unit. The connection device further comprises two patient-side fluid guide units, namely a patient-side inspiration fluid guide unit and a patient-side expiration fluid guide unit. In addition, the connection device comprises two valve devices, namely an inspiration valve device and an expiration valve device. In other words: The fluid circuit arrangement comprises an inspiration connection device according to the invention and an expiration connection device according to the invention. Both connection devices according to the invention connect the medical device with the patient-side coupling unit.

The gas flows at least temporarily along the following fluid circuit:

from the medical device through the source-side inspiration fluid guide unit, the inspiration valve device, and the patient-side inspiration fluid guide unit to the patient-side coupling unit; and from the patient-side coupling unit through the patient-side expiration fluid guide unit, the expiration valve device, and the source-side expiration fluid guide unit to the medical device.

Preferably, a fluid conveying device establishes and keeps a flow of gas in this fluid circuit.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

The present invention is used in the exemplary embodiment to artificially ventilate a patient Pt. A patient-side coupling unit 9, for example, a breathing mask or a tube or a catheter, is attached at or in or on the body of the patient Pt.

Figure 1:
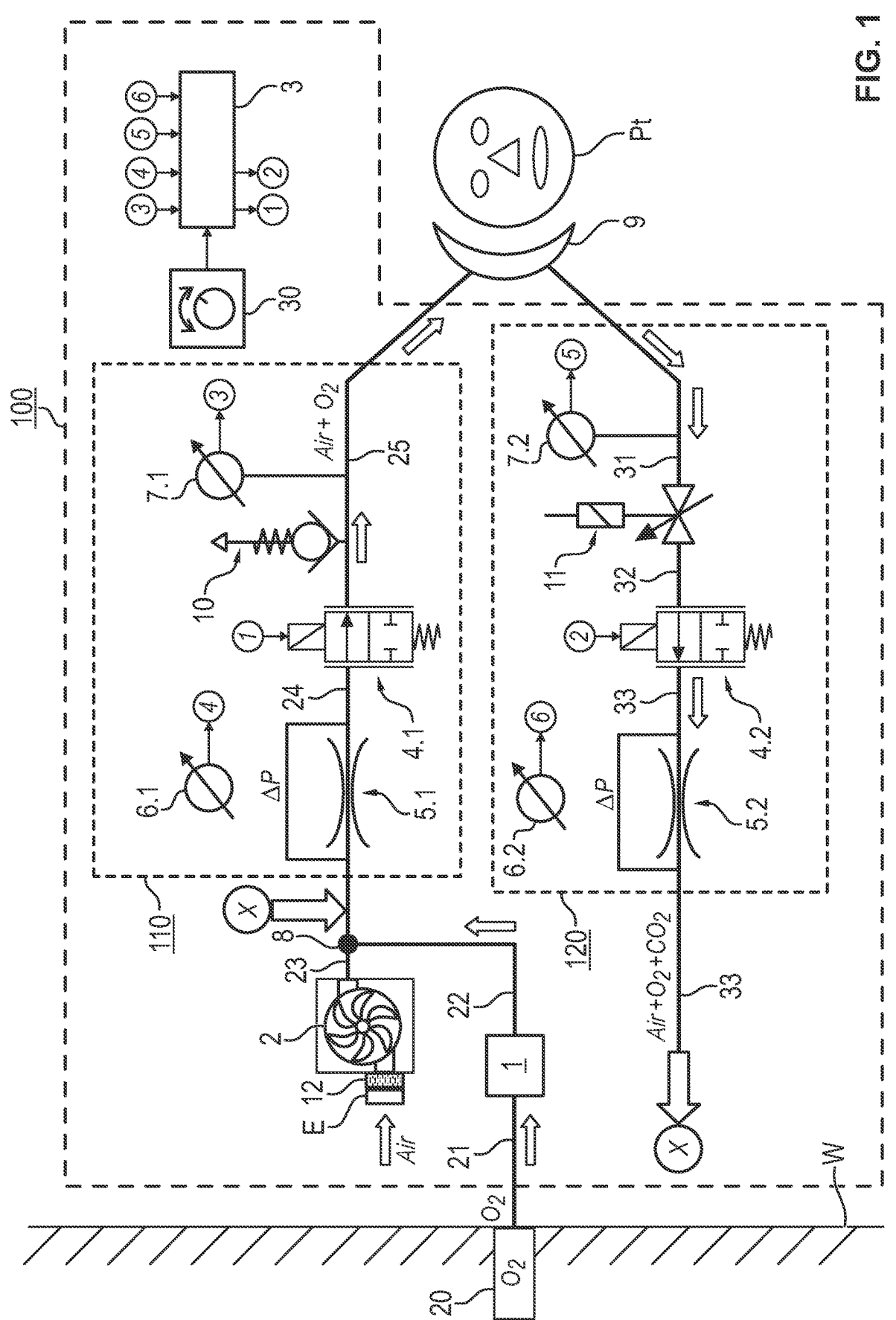
FIG. 1 is a schematic view showing the artificial ventilation of a patient, wherein the present invention is applied twice.

FIG. 1 schematically shows an example for artificially ventilating the patient Pt. A ventilator 100, shown only schematically, carries out a sequence of ventilation strokes and delivers a respective quantity of a gas to the patient-side coupling unit 9 and hence to the patient Pt during each ventilation stroke. This gas contains a percentage (vol. %) of oxygen. A user presets a desired percentage of oxygen in the gas. For example, the user sets the desired oxygen content manually by means of a rotary knob 30. This oxygen content may be above the oxygen content in the breathing air. To increase the oxygen content compared to the breathing air, a gas comprising breathing air and pure oxygen is generated in the exemplary embodiment.

The connection device according to the present invention is used twice in the example according to FIG. 1, namely, in an inhalation (inspiration) connection device 110 and in an exhalation (expiration) connection device 120. The gas comprising oxygen is fed through an inhalation duct of the inhalation connection device 110 to the patient-side coupling unit 9. Breathing air, which was exhaled by the patient Pt, is discharged from the patient-side coupling unit 9 through an exhalation duct of the exhalation connection device 120. The two connection devices 110, 120 are preferably connected to the patient-side coupling unit 9 via a Y-piece. The exhalation duct leads into the surrounding area or to a stationary fluid receptacle (not shown) in one embodiment.

A blower 2 or another fluid conveying unit (fluid delivery unit) sucks ambient air through an inlet E. A filter 12 filters particles and harmful substances out of the ambient air suctioned.

A supply port 20 provides pure oxygen. The supply port 20 is stationary in the exemplary embodiment and is arranged in a wall W and it supplies the pure oxygen with a pressure that is between 2 bar and 5 bar.

A gas of pure oxygen and breathing air is generated or is formed at a mixing point 8. The supply port 20 provides the pure oxygen and the blower 2 provides the breathing air.

It is possible that a mixture of at least one anesthetic and a carrier gas is generated by an anesthetic evaporator and the latter feeds this mixture into the inhalation duct. The gas, which is delivered to the patient-side coupling unit 9, comprises in this embodiment oxygen as well as at least one anesthetic. The patient Pt is anesthetized or sedated thereby.

In one embodiment, the blower 2 generates in the section of the inhalation duct between the mixing point 8 and the patient-side coupling unit 9 a pressure that is between 20 mbar and 100 mbar and preferably between 30 mbar and 60 mbar and which is constant over time in one embodiment, of course, aside from inevitable fluctuations based on the operation of the blower 2. In another embodiment, the pressure and/or the volume flow, which is generated by the blower 2, is controlled with the control gain of following a predefined time course.

In addition, the following components of the ventilator 100 are arranged in the inhalation duct:

a pressure reducer 1, an actuated and controlled inhalation proportional valve 4.1, which acts as a valve device according to the present invention, a pneumatic resistance 5.1, a volume flow sensor 6.1, a pressure sensor 7.1 and an overpressure (pressure relief) valve 10.

A pressure reducer is defined as a component that has a pre (admission, intake) pressure inlet and a back (exit) pressure outlet, wherein the pressure at the back pressure outlet is at most equal to the pressure at the pre-pressure inlet and is, in addition, at most equal to an upper pressure threshold, which is predefined by the construction of the pressure reducer.

A line 21 leads from the supply port 20 for pure oxygen to an inlet of the pressure reducer 1. A line 22 leads from an outlet of the pressure reducer 1 to the mixing point 8. A line 23 leads from an outlet of the blower 2 to the mixing point 8. A line 24 leads from the mixing point 8 to the inhalation proportional valve 4.1. A line 25 leads from the inhalation proportional valve 4.1 to the patient-side coupling unit 9. The lines 21 through 25 belong to the inhalation duct of the exemplary embodiment. The line 24 acts as a source-side fluid guide unit arranged upstream, and the line 25 acts as a patient-side fluid guide unit of the inhalation connection device 110, which fluid guide unit is arranged downstream.

The volume flow sensor 6.1 measures an indicator of the volume flow through the inhalation duct and upstream of the inhalation proportional valve 4.1, namely, through the line 24. To measure the volume flow, the volume flow sensor 6.1 measures the pressure difference ΔP upstream and downstream of the pneumatic resistance 5.1 and derives the volume flow in the inhalation duct 21 through 25. The pressure sensor 7.1 measures the pressure in the inhalation duct 21 through 25, downstream of the inhalation proportional valve 4.1 and in the line 25 in the exemplary embodiment. The pressure relief valve 10 opens when the pressure in the line 25 exceeds a predefined threshold, and it reduces thereby the pressure in the line 25.

The pneumatic resistance 5.1 is arranged upstream of the inhalation proportional valve 4.1 in the example shown. It is also possible that the inhalation proportional valve 4.1 is arranged upstream of the pneumatic resistance 5.1.

The control device (control unit) 3 receives measured values from the sensors 6.1 and 7.1, processes the measured values and actuates and controls the inhalation proportional valve 4.1 depending on the processed measured values. The control device 3 carries out a closed-loop control with the control gain of having the actual time course of the volume flow in the line 25 follow a predefined desired time course of the volume flow. The volume flow being delivered during the ventilation of the patient Pt may be between 1 L/min and 200 L/min.

It is also possible that the control gain is to have the actual time course of the pressure in the line 25 follow a predefined desired time course.

The following components are arranged in the exhalation duct:

an actuated exhalation proportional valve 4.2, which acts as a valve device,
  a pneumatic resistance 5.2,
  a volume flow sensor 6.2,
  a pressure sensor 7.2 and
  a PEEP valve 11.

PEEP means positive end-expiratory pressure. It is possible that the same component carries out the function of both the exhalation proportional valve 4.2 and of the PEEP valve 11.

A line 31 leads from the patient-side coupling unit 9 to the exhalation proportional valve 4.2. A line 32 leads from the exhalation proportional valve 4.2 to the PEEP valve 11. A line 33 leads from the PEEP valve 11 into the surrounding area or back to the inhalation duct 21 through 25. The lines 31 through 33 belong to the exhalation duct, through which exhaled air is sent. The line 31 acts as a patient-side fluid guide unit arranged upstream, and the line 33 acts as a source-side fluid guide unit of the exhalation connection device 120, which [fluid guide unit] is arranged downstream.

If the exhaled air is sent through the exhalation duct 31 through 33 back to the inhalation duct 21 through 25, a closed ventilation circuit is formed. The return is shown schematically in FIG. 1.

The exhalation proportional valve 4.2, the pneumatic resistance 5.2 and the sensors 6.2 and 7.2 are configured in the same manner as the corresponding components in the inhalation duct 21 through 25. The PEEP valve 11 ensures that the end-expiratory pressure in the lungs of the patient Pt does not drop below a predefined threshold.

Figure 2:
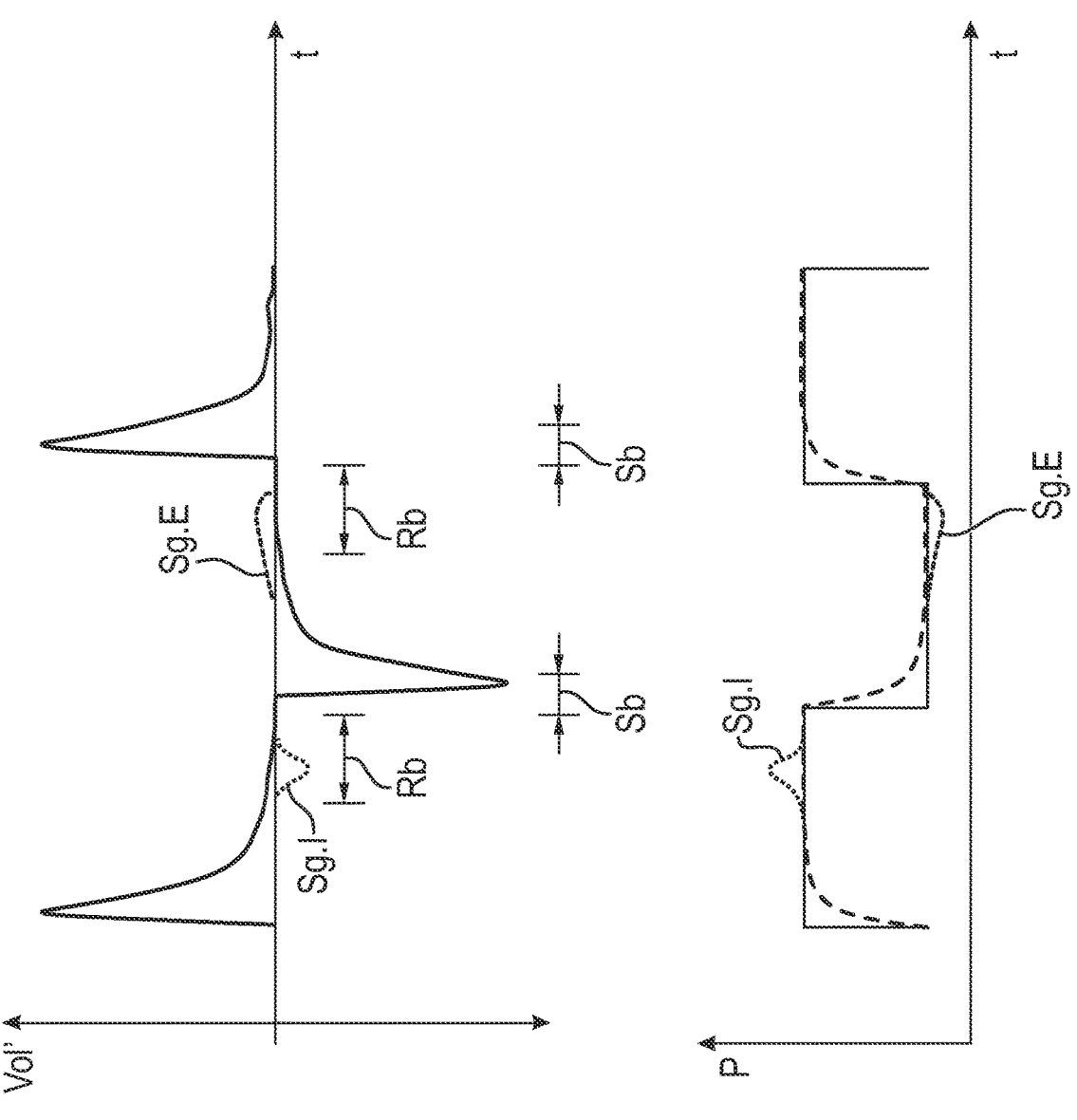
FIG. 2 is a view showing exemplary time courses of the volume flow and of the pressure during the artificial ventilation.

Both the volume flow, i.e., the flow of gas per unit of time through the inhalation duct 21 through 25 to the patient-side coupling unit 9 and the volume flow from the patient-side coupling unit 9 through the exhalation duct 31 through 33 can each follow a respective predefined time course in the exemplary embodiment. FIG. 2 shows in its top part an exemplary required time course of the volume flow (Vol') and in its bottom part an exemplary required time course of the pressure (P). Values above the x axis mean a flow of the gas towards the patient Pt (inhalation), and values under the x axis show a flow away from the patient Pt (exhalation). FIG. 2 shows in its bottom part a desired time course of the pressure P with solid lines and the actualtime course of the pressure P with broken lines.

A pre-pressure and a back pressure are present at the two respective proportional valves 4.1 and 4.2. The pre-pressure at the inhalation proportional valve 4.1 is the pressure in the line 24, and the back pressure is the pressure in line 25. The pre-pressure at the exhalation proportional valve 4.2 is the pressure in the line 32, and the back pressure is the pressure in line 33. The back pressure is lower than or at most equal to the pre-pressure.

FIG. 2 shows a range of control over time, Rb, and a switching range over time, Sb. The pre-pressure and the back pressure differ from one another in a switching range Sb, and the valve is opened rapidly in order to reduce this pressure difference rapidly. As a rule, a higher volume flow Vol' occurs in a switching range Sb. The pre-pressure and the back pressure differ from one another only relatively slightly in a range of control Rb, and the control pressure at the valve 4.1, 4.2 is controlled. As a rule, only a low volume flow Vol' occurs in a range of control Rb.

As a rule, the exhalation proportional valve 4.2 is closed during the inhalation phase, and the time course of the volume flow Vol' is controlled by the inhalation proportional valve 4.1. Conversely, the inhalation proportional valve 4.1 is closed and the time course Vol' is controlled by the exhalation proportional valve 4.2 during the exhalation phase. Two exceptions are suggested in FIG. 2. A disturbance variable Sg.I acts on the volume flow Vol' and on the pressure during the inhalation phase. The disturbance variable Sg.I results, for example, from the circumstance that a relatively great difference occurs between the pre-pressure and the back pressure at the inhalation proportional valve 4.1 during the inhalation phase or that the patient Pt is coughing. The disturbance variable Sg.E results, for example, from the circumstance that the patient Pt is inhaling spontaneously. In order to compensate for the influence of the disturbance variable Sg.I, the control device 3 causes the exhalation proportional valve 4.2 to open briefly during the exhalation phase as well. The control device 3 correspondingly causes the inhalation proportional valve 4.1 to open briefly during the exhalation phase as well in order to compensate for the disturbance variable Sg.E.

FIG. 3 through FIG. 6 show four exemplary embodiments of the inhalation proportional valve 4.1. The exhalation proportional valve 4.2 may have a corresponding configuration. The inhalation proportional valve 4.1 comprises in these embodiments two valves 40.1 and 40.2, which are connected in parallel, and, in the embodiment according to FIG. 6, additionally a third valve 40.3, which is connected in parallel to the valves 40.1 and 40.2. Each valve 40.1, 40.2, 40.3 comprises an ideally round valve seat (crater) 41.1, 41.2, 41.3 made of a rigid material,
  a closure in the form of a flexible membrane or of a rigid plate 42.1, 42.2, 42.3, as well as
  a flexible seal 43.1, 43.2, 43.3.
  Thanks to the flexible seal 43.1, 43.2, 43.3, the closure 42.1, 42.2, 42.3 is movable relative to the valve seat 41.1,

41.2, 41.3. The closure 42.1, 42.2, 42.3 acts as a valve body, and the valve seat 41.1, 41.2, 41.3 acts as a valve body seat.

A first feed line 24.1 leads from the line 24 to the valve seat 41.1, a second feed line 24.2 leads from the line 24 to the valve seat 41.2, and a third feed line 24.3 leads from the line 24 to the valve seat 41.3. A pre-pressure is present from one side, at the bottom in the examples shown, at the closure 42.1, 42.2, 42.3. The respective pre-pressure is equal in one embodiment to the pressure in the feed line 24.1, 24.2, 24.3. The side of the valve seat 41.1, 41.2, 41.3 which points towards the feed line 24.1, 24.2, 24.3, acts as the pre-pressure-side coupling point of the valve 40.1, 40.2, 40.3. The pressure in the feed line 24.1, 24.2, 24.3 and hence the pre-pressure depend on the pressure in the line 24, which leads to the inhalation proportional valve 4.1. In one embodiment, the pressure is equal in the lines 24, 24.1, 24.2, 24.3.

From the other side, a control pressure is present at the closure 42.1, 42.2, 42.3, namely, from the top in the examples shown. The seal 43.1, 43.2, 43.3 belongs to a control pressure-side coupling point of the valve 40.1, 40.2, 40.3. At least two control pressures present may differ from one another. Different embodiments differ from one another, among other things, in how this control pressure is generated and changed when needed.

A first discharge line 25.1 leads from the gap between the closure 42.1 and the valve seat 41.1 to the line 25, a second discharge line 25.2 leads from the gap between the closure 42.2 and the valve seat 41.2 to the line 25, and a third discharge line 25.3 leads from the gap between the closure 42.3 and the valve seat 41.3 to the line 25 The gap 50.1, 50.2, 50.3 between the closures 42.1, 42.2, 42.3 and the respective valve seats 41.1, 41.2, 41.3 belongs to the back pressure-side coupling point of the valve 40.1, 40.2, 40.3.

If the control pressure is higher than the pre-pressure, then the closure 42.1, 42.2, 42.3 is pressed onto the valve seat 41.1, 41.2, 41.3 and it closes this valve seat 41.1, 41.2, 41.3, doing so ideally completely. If, by contrast, the pre-pressure is higher than the control pressure, the closure 42.1, 42.2, 42.3 is moved away from the valve seat 41.1, 41.2, 41.3. As a result, a volume flow takes place through the gap between the valve seat 41.1, 41.2, 41.3 and the closure 42.1, 42.2, 42.3. This volume flow leads to a back pressure in the line 25.1, 25.2, 25.3. In one embodiment, this back pressure is equal to the pressure in the line 25. The volume flow depends on the effective cross-sectional area between the closure 42.1, 42.2, 42.3 and the valve seat 41.1, 41.2, 41.3.

It will be explained below why at least two valves connected in parallel with a respective valve seat each, with a closure and with a seal are used according to the present invention rather than a single valve only. As was already described, the required volume flow can vary between 1 L/min and 200 L/min. This great variation notwithstanding, the time course of the actual volume flow shall differ only slightly from a required time course. This control gain is accomplished by a closed-loop control. It may happen precisely in case of a relatively low volume flow that the distance 50.1, 50.2, 50.3 between the closure 42.1 42.2, 42.3 and the valve seat 41.1, 41.2, 41.3 varies over the circumference of the closure and/or that the closure vibrates or "dances" on the valve seat, similarly to a lid on a pot, which is filled with boiling water. This may lead to a variation, for example, oscillation, of the time course of the actual volume flow in an undesired manner, and/or to said time course not being able to be measured in a reliable manner. The inventors found in experiments that this undesired effect occurs more rarely and in a less intensive manner when at least two parallel valves are used than when only a single valve is used.

Figure 3:
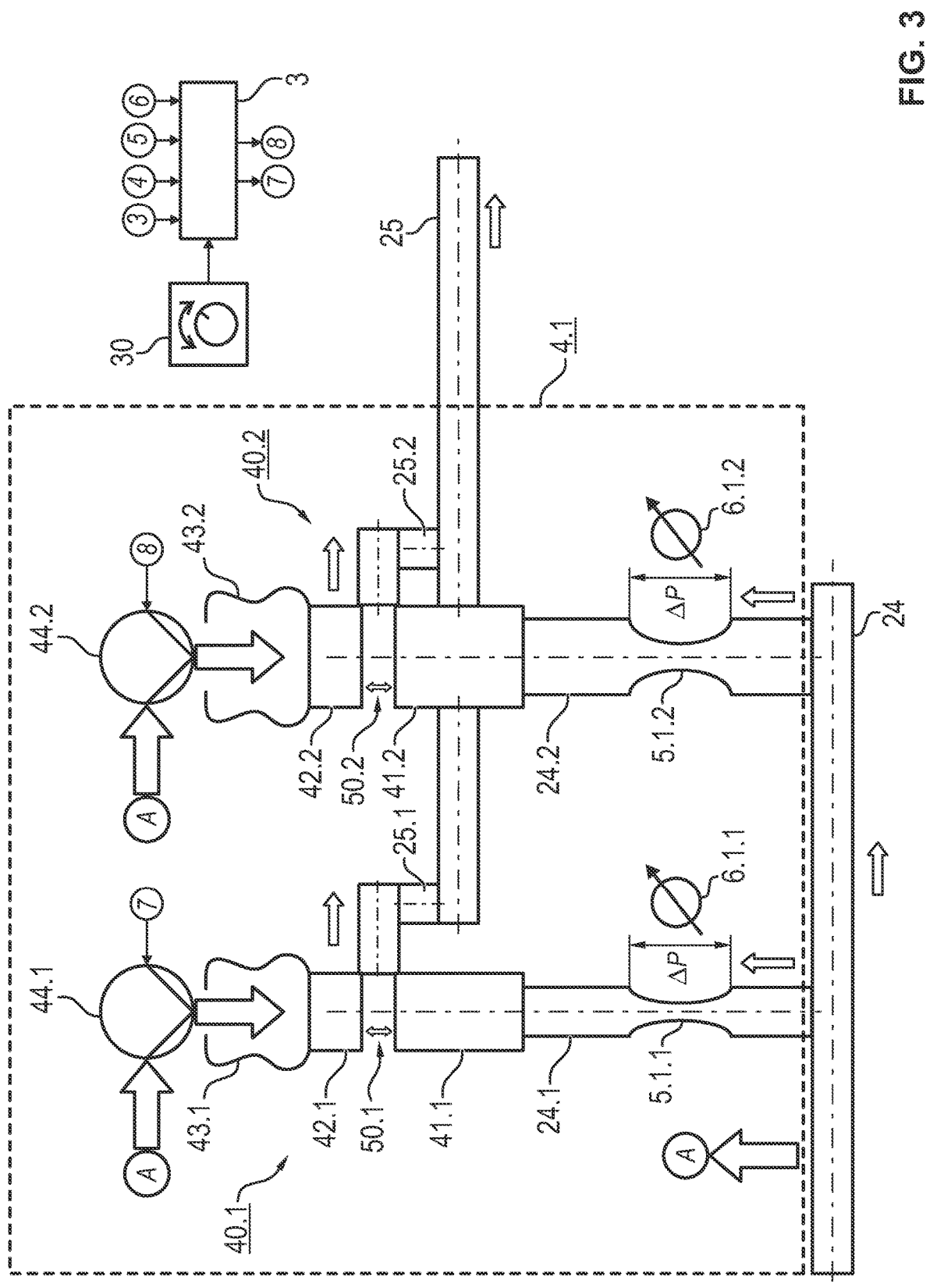
FIG. 3 is a schematic view showing two valves of different sizes, which are connected in parallel, in which two pumps connected in parallel bring about the two control pressures.
Figure 4:
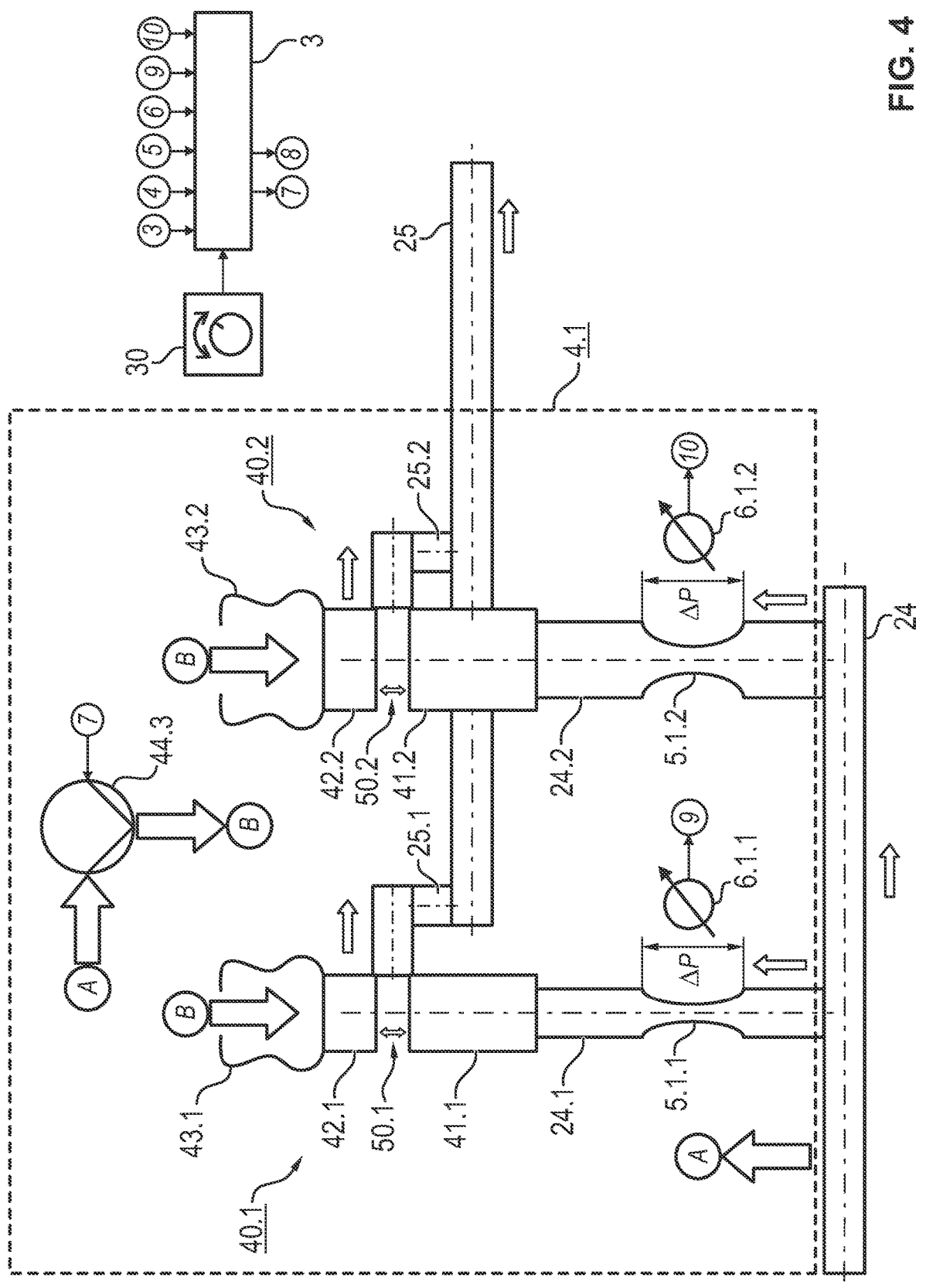
FIG. 4 is a schematic view showing two valves of an equal size, which are connected in parallel, and in which an actuated pump generates the two control pressures.
Figure 5:
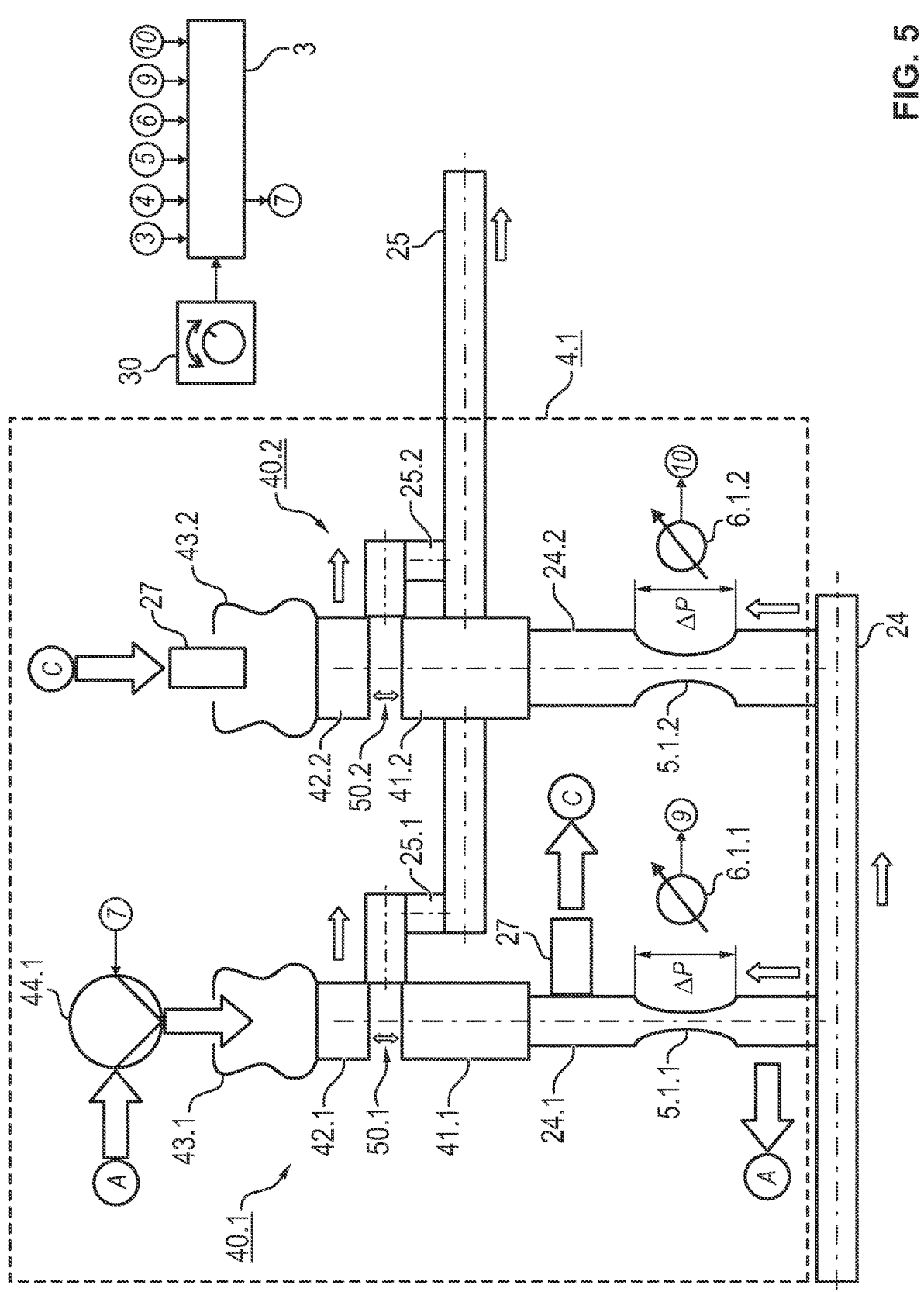
FIG. 5 is a schematic view showing two parallel-connected valves, which have different sizes, and in which an actuated pump generates the control pressure for the smaller valve and the control pressure for the larger valve is branched off.

The valve seat 41.1 has a smaller diameter than the valve seat 41.2 in the examples shown in FIG. 3 and FIG. 5. The closure 42.1 correspondingly has a smaller diameter than does the closure 42.2. The valve 40.1 will therefore be called the "smaller valve" and the valve 40.2 the "larger valve" below. Both valve seats 41.1, 41.2 have the same diameter in the example shown in FIG. 4, and the closure 42.1 and the closure 42.2 likewise have the same diameter. The two valve seats 41.2 and 41.3 have the same diameter in the example shown in FIG. 6, and this identical diameter is smaller than the diameter of the valve seat 41.1.

In the embodiment according to FIG. 3, the inhalation proportional valve 4.1 additionally comprises two fluid conveying units in the form of two actuatable pumps 44.1 and 44.2. The control device 3 is capable of actuating the two pumps 44.1 and 44.2 independently from one another.

Both pumps 44.1, 44.2 are in connection on the inlet side with the line 24. The pressure in the line 24 is equal—aside from inevitable leaks and other pressure drops—to the pressure that is generated by the blower 2 at the outlet thereof. The pump 44.1 generates on the outlet side the control pressure for the smaller valve 40.1, and the pump 44.2 generates the control pressure for the larger valve. The effect of the pump 44.1 is that the control pressure, which is present at the smaller valve 40.1, is higher or also lower than the pressure in the line 24 and hence higher or lower than the pressure that is generated by the blower 2. For example, the blower 2 generates a pressure of 30 mbar constantly, and the pump 44.1 increases or decreases this pressure by a maximum of 20 mbar depending on the actuation, so that the control pressure is between 10 mbar and 50 mbar at the smaller valve 40.1. The pump 44.2 operates in the same manner. Since the control pressure-side coupling point of the valve 40.1, 40.2 is in a fluid connection with the line 24, it is not necessary for the pump 44.1, 44.2 to generate the control pressure alone, and the control pressure is rather generated by a superimposition of the pressure in the line 24 and the pressure at the outlet of the pump 44.1, 44.2.

In one embodiment, a respective characteristic is predefined for each valve 40.1, 40.2 and is stored in a computer-analyzable form. The control device 3 automatically analyzes the respective characteristic in order to actuate the pump 44.1, 44.2. The characteristic indicates the control pressure to be reached as a function of the volume flow to the valve 40.1, 40.2. The characteristic may depend on the pressure that is generated by the blower 2.

Figure 7:
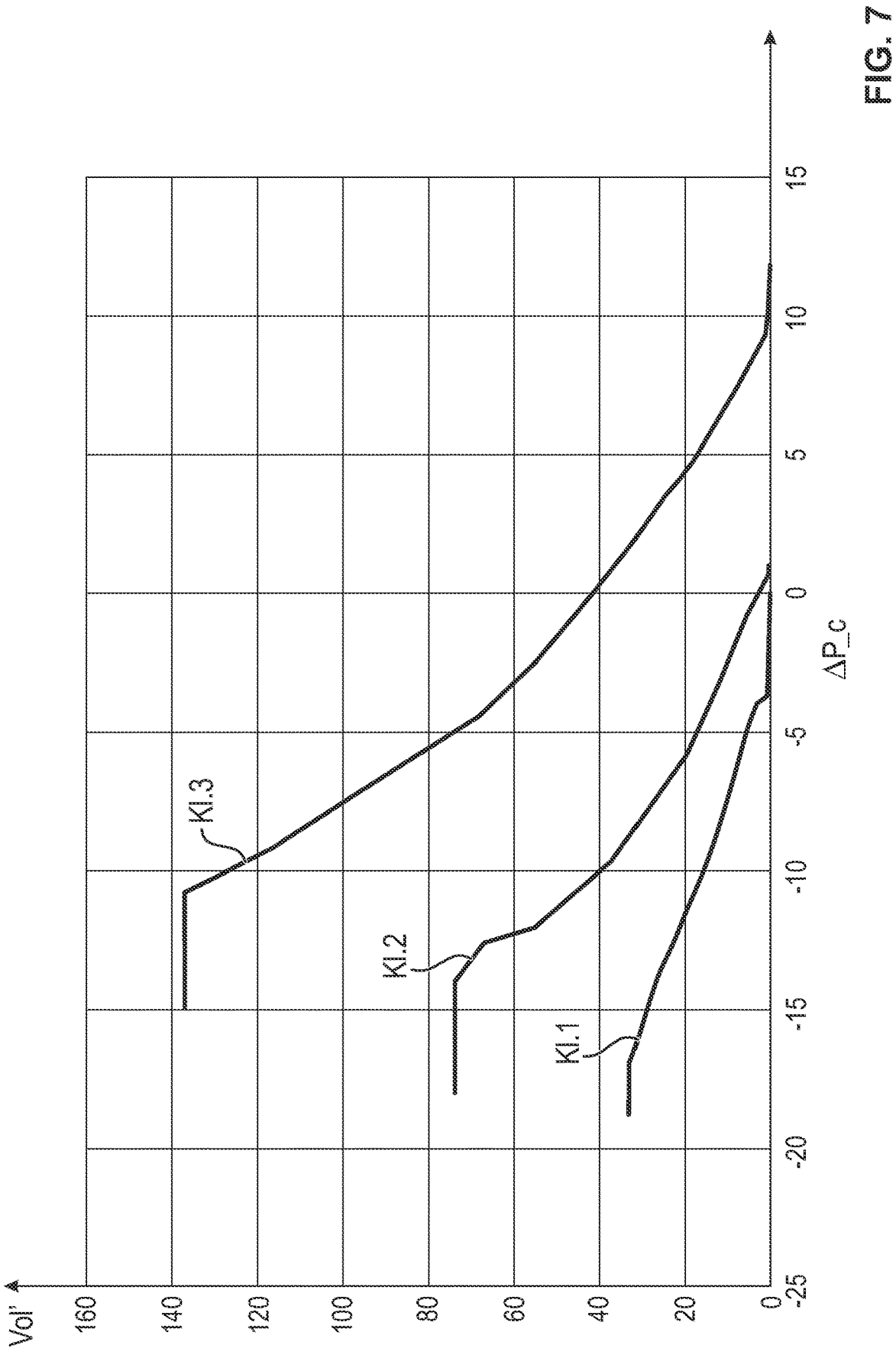
FIG. 7 is a graph showing three exemplary characteristics for three valves of different sizes, which characteristics each show the control pressure depending on the volume flow.

FIG. 7 shows as an example three characteristics K1.1, K1.2, K1.3 for three different valves V.1, V.2, V.3, which have the same configuration as the two valves 40.1 and 40.2 and are connected in parallel. The valve seat of the valve V.3 has a larger diameter than does the valve seat of the valve V.2, and the valve seat of the valve V.2 has a larger diameter than the valve seat of the valve V.1. The volume flow in [L/min] is plotted on the y axis, and the difference $\Delta P\_c$ that can be obtained between the control pressure and the pre-pressure is plotted on the x axis. At a difference of $\Delta P\_c > 0$, the control pressure is higher than the pressure, and the valve is closed or is at least largely closed. Consequently, all three valves are opened in case of a high-volume flow in this example, and only two valves are open or even only one valve is open in case of a low volume flow.

Figure 6:
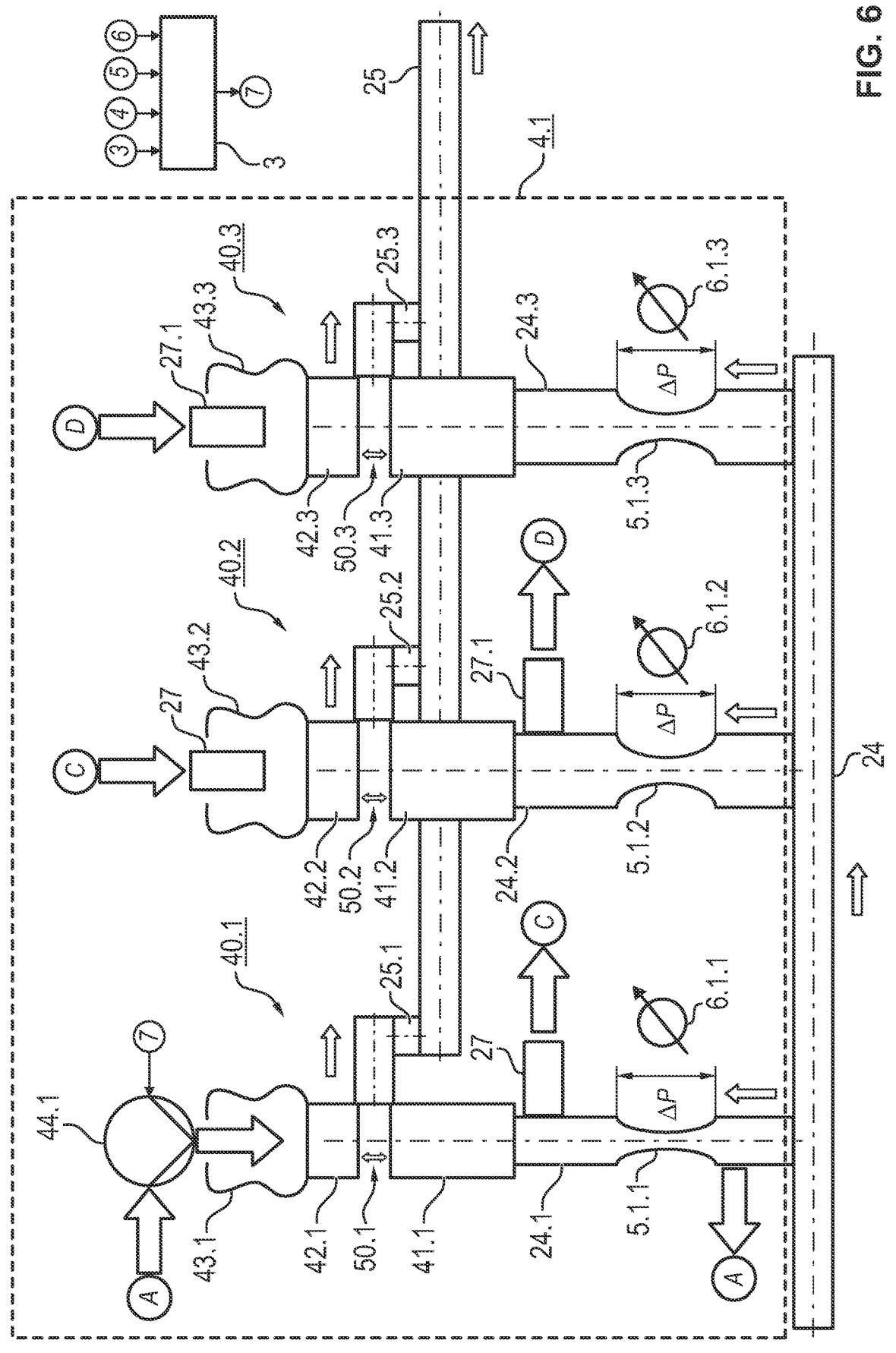
FIG. 6 is a schematic view showing a variant of the embodiment according to FIG. 5, in which a third valve is connected in parallel.

A respective working range is predefined in the example according to FIG. 3 and FIG. 6 for each valve 40.1 and 40.2, namely, a working range from a1 [L/min] to b1 [L/min] for the smaller valve 40.1 and a working range from a2 [L/min] to b2 [L/min] for the larger valve 40.2. The working range from a2 [L/min] to b2 [L/min] is likewise predefined for the third valve 40.3 in the example shown in FIG. 6. Each working range is a partial range of the range for the possible volume flow to the valve 40.1, 40.2. The working range for the smaller valve 40.1 is located to the left of the working range for the larger valve 40.2, i.e., a1<a2 and b1<b2. The two working ranges preferably overlap each other, i.e., a2>b1. The smaller valve 40.1 is closed when the volume flow in the line 24 is outside of the working range from a1 [L/min] to b1 [L/min], especially at a high-volume flow. The larger valve 40.2 and the third valve 40.3 are closed when the volume flow in the line 24 is outside of the working range from a2 [L/min] to b2 [L/min], i.e., in case of a low volume flow. Furthermore, a characteristic that indicates the respective control pressure to be reached is predefined for each working range in the example shown in FIG. 3. The control device 3 actuates the two pumps 44.1 and 44.2 correspondingly.

In one embodiment, the control device 3 uses the volume flow Vol' in the line 24, which was measured by the volume flow sensor 6.1, and actuates the two pumps 44.1 and 44.2 as a function of the characteristics stored. The control device 3 controls in another embodiment the respective control pressure, which is present at the valves 40.1 and 40.2. The volume flow sensor 6.1, which was mentioned already, therefore measures, on the one hand, the volume flow in the line 24. A volume flow sensor 6.1.1 measures the volume flow in the feed line 24.1 from the line 24 to the smaller valve 40.1, and a volume flow sensor 6.1.2 measures the volume flow in the feed line 24.2 from line 24 to the larger valve 40.2. Two pneumatic resistances 5.1.1 and 5.1.2 are therefore arranged in the two feed lines 24.1 and 24.2 to the valves 40.1 and 40.2 in one embodiment, and the volume flow sensor measures the pressure difference as an indicator of the volume flow. The embodiment with a plurality of volume flow sensors generates redundancy and/or makes an error correction possible, because the volume flow in the line 24, which is measured by the sensor 6.1, is ideally equal to the sum of the volume flows from line 24 to the two valves 40.1 and 40.2, which volume flows are measured by the sensors 6.1.1 and 6.1.2.

The control pressures for the two valves 40.1 and 40.2 can be set in the same manner when the two valves 40.1 and 40.2 have valve seats and closures having the same diameter. The two control pressures may be equal. It is also possible that the control pressures are different for valves 40.1, 40.2 of equal size.

FIG. 4 shows a variant in which the two valves 40.1 and 40.2 are of equal size, i.e., have valve seats 41.1, 41.2 of equal size and closures 42.1, 42.2 of equal size. In addition, the same control pressure is always present at both valves in the embodiment shown. This effect is achieved because a single actuated pump 44.3 is used instead of two pumps 44.1 and 44.2 connected in parallel. This one pump 44.3 generates both the control pressure for the valve 40.1 and the control pressure for the valve 40.2. The inlet of the pump 44.3 is, in turn, in a fluid connection with the line 24. The control device 3 actuates the pump 44.3.

Only one actuated pump 44.1 is likewise used in the embodiment according to FIG. 5. Just as in FIG. 3, the valve 40.1 is smaller than the valve 40.2. Different control pressures are nevertheless present, as a rule, at the two valves 40.1 and 40.2. The pump 44.1 changes the pressure in the line 24 and thereby generates the control pressure for the smaller valve 40.1, as this was described in reference to FIG.

3. In the embodiment shown, a line 27, which is suggested only schematically, connects the feed line 24.1 guiding to the smaller valve 40.1 to the control pressure-side inlet of the larger valve 40.2. The control pressure, which is present at the larger valve 40.2, is lower than the pre-pressure that is present at the smaller valve 40.1, being namely reduced by the pressure reduction based on the pneumatic resistance 5.1.1 and on the flow through the line 27. The control pressure is, for example, $$P\_c = P\_v - R(5.1.1)*Vol'(27),$$

wherein P_c is the control pressure at the larger valve 40.2, P_v is the pre-pressure at the smaller valve 40.1, R(5.1.1) is the pneumatic resistance of the line 27 and Vol'(27) is the volume flow through the line 27. A high-volume flow through the feed line 24.1 also leads to a high-volume flow through the line 27 and hence to a low control pressure at the larger valve 40.2, which will therefore open wider. This leads, in turn, to a higher volume flow from the larger valve 40.2 into the line 25.

In the embodiments that are shown in FIG. 3 through FIG. 5, the inhalation proportional valve 4.1 comprises two parallel-connected valves 40.1 and 40.2. It is also possible that the inhalation proportional valve 4.1 comprises three or even more valves connected in parallel. The valve seats of these valves may have diameters of an equal size or at least two different diameters. The exhalation proportional valve 4.2 preferably also comprises at least two valves connected in parallel.

The embodiment according to FIG. 6 expands the embodiment according to FIG. 5 by a third valve 40.3. A line 27.1 leads from the feed line 24.2 to the control pressure-side coupling point of the third valve 40.3. The control pressure, which is present at the third valve 40.3, is lower than the pre-pressure that is present at the central valve 40.2, namely, being reduced by the pressure reduction occurring based on the pneumatic resistance 5.1.2 and on the flow through the line 27.1.

While specific embodiments of the invention have been shown and described in detail to illustrate the application of the principles of the invention, it will be understood that the invention may be embodied otherwise without departing from such principles.

| | List of Reference Characters: |
|---|---|
| 1 | Pressure reducer, connected to the supply port 20 on the inlet side and to the line 22 on the outlet side |
| 2 | Blower of the ventilator 100; it has the inlet E |
| 3 | Signal-processing control device; it actuates the proportional valves 4.1 and 4.2 as well as the pumps 44.1, 44.2, 44.3 |
| 4.1 | Proportional valve in the inhalation duct 21 through 25, actuated by the control device 3; it comprises the valves 40.1, 40.2, 40.3 |
| 4.2 | Proportional valve in the exhalation duct 31 through 33, actuated by the control device 3 |
| 5.1 | Pneumatic resistance in the inhalation duct 21 through 25 |
| 5.1.1 | Pneumatic resistance upstream of the smaller valve 40.1 |
| 5.1.2 | Pneumatic resistance upstream of the larger valve 40.2 |
| 5.1.3 | Pneumatic resistance upstream of the third valve 40.3 |
| 5.2 | Pneumatic resistance in the exhalation duct 31 through 33 |
| 6.1 | Volume flow sensor; it measures the pressure difference ΔP upstream and downstream of the pneumatic resistance 5.1 and derives the volume flow in the line 24 of the inhalation duct 21 through 25 |
| 6.1.1 | Volume flow sensor; it measures the pressure difference ΔP upstream and downstream of the pneumatic resistance 5.1.1 and derives the volume flow through the feed line 24.1 to the smaller valve 40.1 |
| 6.1.2 | Volume flow sensor; it measures the pressure difference ΔP upstream and downstream of the pneumatic resistance 5.1.2 and |

-continued

| List of Reference Characters: | |
|---|---|
| | derives the volume flow through the feed line 44.2 to the larger valve 40.2 |
| 6.1.3 | Volume flow sensor; it measures the pressure difference ΔP upstream and downstream of the pneumatic resistance 5.1.3 and derives the volume flow through the feed line 44.3 to the third valve 40.3 |
| 6.2 | Volume flow sensor; it measures the pressure difference ΔP upstream and downstream of the pneumatic resistance 5.2 and derives the volume flow in the exhalation duct 31 through 33 |
| 7.1 | Pressure sensor; it measures the pressure in the inhalation duct 21 through 25 |
| 7.2 | Pressure sensor; it measures the pressure in the exhalation duct 31 through 33 |
| 8 | Mixing point, into which the lines 22 and 23 lead and in which breathing air is mixed with pure oxygen |
| 9 | Patient-side coupling unit, connected to the patient Pt and to the ventilator 100 |
| 10 | Pressure relief valve in the inhalation duct 21 through 25 |
| 11 | PEEP valve in the exhalation duct 31 through 33 |
| 12 | Filter between the inlet E and the blower 2 |
| 20 | Supply port in the wall W for pure oxygen |
| 21 | Line from the supply port 20 to the pressure reducer 1 |
| 22 | Line from the pressure reducer 1 to the mixing point 8 |
| 23 | Line from the blower 2 to the mixing point 8 |
| 24 | Line from the mixing point 8 to the inhalation proportional valve 4.1 |
| 24.1 | First feed line; it leads from the line 24 to the pre-pressure-side coupling point of the smaller valve 40.1 |
| 24.2 | Second feed line; it leads from the line 24 to the pre-pressure-side coupling point of the larger valve 40.2 |
| 24.3 | Third feed line; it leads from the line 24 to the pre-pressure-side coupling point of the third valve 40.3 |
| 25 | Line from the inhalation proportional valve 4.1 to the patient-side coupling unit 9 |
| 25.1 | First discharge line; it leads from the back pressure-side coupling point of the smaller valve 40.1 to the line 25 |
| 25.2 | Second discharge line; it leads from the back pressure-side coupling point of the larger valve 40.2 to the line 25 |
| 25.3 | Third discharge line; it leads from the back pressure-side coupling point of the third valve 40.3 to the line 25 |
| 27 | Line from the feed line 24.1 to the control pressure-side coupling point of the larger valve 40.2 |
| 27.1 | Line from the feed line 24.2 to the control pressure-side coupling point of the third valve 40.3 |
| 30 | Rotary knob, which a user can turn in order to preset the required percentage of oxygen in the gas, which is delivered to the patient-side coupling unit 9 |
| 31 | Line from the patient-side coupling unit 9 to the exhalation proportional valve 4.2 |
| 32 | Line from the exhalation proportional valve 4.2 to the PEEP valve 11 |
| 33 | Line from the PEEP valve 11 into the surrounding area or to the inhalation duct 21 through 25 |
| 40.1 | Smaller valve; it comprises the valve seat 41.1, the membrane 42.1 and the seal 43.1 |
| 40.2 | Larger valve; it comprises the valve seat 41.2, the membrane 42.2 and the seal 43.2 |
| 40.3 | Third valve; it comprises the valve seat 41.3, the membrane 42.3 and the seal 43.3 |
| 41.1 | Valve seat (crater) of the smaller valve 40.1 |
| 41.2 | Valve seat (crater) of the larger valve 40.2 |
| 41.3 | Valve seat (crater) of the third valve 40.3 |
| 42.1 | Closure in the form of a membrane or plate of the smaller valve 40.1; it defines the back pressure-side coupling point |
| 42.2 | Closure in the form of a membrane or plate of the larger valve 40.2; it defines the back pressure-side coupling point |
| 42.3 | Closure in the form of a membrane or plate of the third valve 40.3; it defines the back pressure-side coupling point |
| 43.1 | Seal of the smaller valve 40.1; it defines the control pressure-side coupling point |
| 43.2 | Seal of the larger valve 40.2; it defines the control pressure-side coupling point |
| 43.3 | Seal of the third valve 40.3; it defines the control pressure-side coupling point |
| 44.1 | Actuated first pump; it produces the control pressure for the smaller valve 40.1 |
| 44.2 | Actuated second pump; it produces the control pressure for the |

-continued

| List of Reference Characters: | |
|---|---|
| | larger valve 40.2 |
| 44.3 | Actuated shared pump; it produces the control pressure for both valves 40.1 and 40.2 |
| 100 | Ventilator; it maintains a closed ventilation circuit in the closed ventilation circuit with the connection devices 110 and 120 |
| 110 | Inhalation connection device; it sends a gas to the patient-side coupling unit 9 |
| 120 | Exhalation connection device; it removes a gas from the patient-side coupling unit 9 |
| ΔP | Pressure difference at the pneumatic resistance 5.1, 5.1.1, 5.1.2, 5.1.3, 5.2 |
| E | Inlet, through which ambient air flows to the blower 2; it acts as a source of the inhalation duct 21 through 25 |
| K1.1, K1.2, K1.3 | Characteristics, which set the attainable control pressure as a function of the volume flow |
| P | Pressure variable over time in the inhalation duct 21 through 25 and in the exhalation duct 31 through 33 |
| Pt | Patient; the patient is ventilated artificially by the ventilator; carries the patient-side coupling unit 9 |
| Rb | Range of control over time, in which the control pressure at the inhalation proportional valve 4.1 is controlled |
| Sb | Switching range over time, in which the control pressure at the inhalation proportional valve 4.1 is changed by switching |
| Sg.E | Disturbance variable, which acts on the pressure P and on the volume flow Vol' during the exhalation phase |
| Sg.I | Disturbance variable, which acts on the pressure P and on the volume flow Vol' during the inhalation phase |
| Vol' | Volume flow through a line |
| W | Wall; it has the supply port 20 for pure oxygen |

What is claimed is:

1. A connection device for connecting a source or a sink for a gas to a patient-side coupling unit, wherein the patient-side coupling unit is at least temporarily connected to or can be connected to a patient, the connection device comprising:

a source-side fluid guide unit;

a patient-side fluid guide unit;

a valve device comprising a first valve and a second valve; and a signal-processing control unit, wherein the source-side fluid guide unit is configured to establish at least temporarily a fluid connection between the source or the sink and the valve device and the patient-side fluid guide unit is configured to establish at least temporarily a fluid connection between the patient-side coupling unit and the valve device, the first valve and the second valve being connected in parallel and the first valve and the second valve being arranged between the source-side fluid guide unit and the patient-side fluid guide unit, wherein the connection device is configured such that the gas flows in a flow direction from the source to the patient-side coupling unit or from the patient-side coupling unit to the sink and flows through the first valve and/or through the second valve with a flow from that one of the fluid guide units which is arranged upstream of the valve device relative to the flow direction into that one of the fluid guide units which is arranged downstream of the valve device;

wherein the control unit is configured to set a respective control pressure at each valve of the valve device and to control, by an open-loop control or a closed-loop control, at least one of a volume flow through that one of the fluid guide units which is arranged downstream of the valve device and a pressure in that one of the fluid guide units which is arranged downstream of the valve device, by setting the respective control pressures at the valves, wherein a control gain of the open-loop control or the closed loop control is to cause at least one of an actual time course of the volume flow through that one of the fluid guide units which is arranged downstream and/or an actual time course of the pressure in that one of the fluid guide units which is arranged downstream to follow a predefined time course, and wherein each valve of the valve device comprises a respective valve body and a valve body seat, wherein the valve body seat is configured such that a fluid can flow through the valve body seat, wherein the valve body is movable relative to the valve body seat, and wherein a cross-sectional area of the valve body seat of one valve of the valve device is smaller than a cross-sectional area of the valve body seat of another valve of the valve device.

2. The connection device in accordance with claim 1, wherein:

a respective pre-pressure is present at each valve of the valve device and the respective pre-pressure depends on the pressure in that one of the fluid guide units which is arranged upstream; and the volume flow through that one of the fluid guide units which is arranged downstream depends on the respective pre-pressure and on the respective control pressure, which are present at the valves of the valve device.

3. The connection device in accordance with claim 1, wherein:

the valve device further comprises a controllable fluid conveying unit associated with at least one valve of the valve device;

the controllable fluid conveying unit is configured to set the control pressure, which is present at the associated valve; and the control unit is configured to set the control pressure at the associated valve by controlling the controllable fluid conveying unit.

4. The connection device in accordance with claim 3, further comprising a volume flow sensor, wherein:

the volume flow sensor is configured to measure an indicator of the volume flow through that one of the fluid guide units, which is arranged upstream of the valve device, to the valve device; and the control unit is configured to control the fluid conveying unit depending on the measured volume flow to the valve device.

5. The connection device in accordance with claim 1, wherein:

each valve comprises: a pre-pressure-side coupling point, a back pressure-side coupling point, and a control pressure-side coupling point;

the pre-pressure-side coupling point is in a fluid connection with that one of the fluid guide units which is arranged upstream;

the back pressure-side coupling point is in a fluid connection with that one of the fluid guide units which is arranged downstream; and the respective control pressure is present at the control pressure-side coupling point.

6. The connection device in accordance with claim 5, wherein:

the pre-pressure-side coupling point of the first valve is in a fluid connection with the control pressure-side coupling point of the second valve.

7. The connection device in accordance with claim 6, wherein:

the valve device further comprises a third valve;

the third valve comprises: a pre-pressure-side coupling point; a back pressure-side coupling point, and a control pressure-side coupling point;

the three valves are connected in parallel and are arranged between the source-side fluid guide unit and the patient-side fluid guide unit; and the pre-pressure-side coupling point of the second valve is in a fluid connection with the control pressure-side coupling point of the third valve.

8. The connection device in accordance with claim 6, wherein:

the valve device further comprises a controllable fluid conveying unit associated with the first valve;

a respective pre-pressure is present at each valve of the valve device and the respective pre-pressure depends on the pressure in that one of the fluid guide units which is arranged upstream;

the controllable fluid conveying unit is configured to set the respective control pressure, which is present at the first valve; and the connection device is configured such that the respective control pressure, which is present at the second valve, is set as a function of the respective pre-pressure and the respective control pressure, which are present at the first valve.

9. The connection device in accordance with claim 1, in combination with a fluid delivery device, the combination forming a portion of a supply arrangement for supplying the patient-side coupling unit with the gas, the gas comprising oxygen, wherein the fluid delivery device is configured to deliver the gas to the patient-side coupling unit such that the gas flows from the source through the source-side fluid guide unit, subsequently through the valve device and subsequently through the patient-side fluid guide unit to the patient-side coupling unit.

10. The connection device in accordance with claim 9, in combination to form the portion of the supply arrangement, further comprising a mixing point, wherein:

the supply arrangement is configured to generate the gas at the mixing point by mixing at least two gas components; and the mixing point provides or serves as a source of the gas.

11. The connection device in accordance with claim 1, wherein:

the connection device forms a portion of a discharging arrangement for discharging the gas from the patient-side coupling unit, the gas comprising oxygen; and the discharging arrangement is configured such that the gas flows from the patient-side coupling unit through the patient-side fluid guide unit, subsequently through the valve device and subsequently through the source-side fluid guide unit to the sink.

12. The connection device in accordance with claim 1, wherein:

the connection device forms a portion of a circuit arrangement for establishing a fluid circuit between a medical device and the patient-side coupling unit;

the connection device comprises the source-side fluid guide unit as a source-side inspiration fluid guide unit and a further source-side fluid guide unit as a source-side expiration fluid guide unit;

the connection device comprises the patient-side fluid guide unit as a patient-side inspiration fluid guide unit and a further patient-side fluid guide unit as a patient-side expiration fluid guide unit;

the connection device comprises the valve device comprising the first valve and the second valve as an inspiration valve device and a further valve device comprising a further first valve and a further second valve as an expiration valve device;

the circuit arrangement is arranged such that a first gas flows from the medical device through the source-side inspiration fluid guide unit, the inspiration valve device and the patient-side inspiration fluid guide unit to the patient-side coupling unit, and a second gas flows from the patient-side coupling unit through the patient-side expiration fluid guide unit, the expiration valve device, and the source-side expiration fluid guide unit to the medical device.

13. A process for connecting a source or a sink for a gas to a patient-side coupling unit, wherein the patient-side coupling unit is at least temporarily connected to a patient, the process comprising the steps of:

providing a connection device comprising: a source-side fluid guide unit; a patient-side fluid guide unit and a valve device comprising a first valve and a second valve, wherein the source-side fluid guide unit at least temporarily establishes a fluid connection between the source or the sink and the valve device, and the patient-side fluid guide unit at least temporarily establishes a fluid connection between the patient-side coupling unit and the valve device, wherein the first valve and the second valve of the valve device are connected in parallel and are arranged between the source-side fluid guide unit and the patient-side fluid guide unit;

guiding the gas to flow in a flow direction from the source to the patient-side coupling unit or from the patient-side coupling unit to the sink, and during the gas flow from that one of the fluid guide units which is arranged upstream of the valve device relative to the flow direction into that one of the fluid guide units which is arranged downstream of the valve device, the gas flowing through the first valve and/or through the second valve;

controlling by an open-loop control or a closed-loop control, at least one of a volume flow through that one of the fluid guide units which is arranged downstream and a pressure in that one of the fluid guide units which is arranged downstream, wherein a control gain of the open-loop control or the closed-loop control is to cause at least one of an actual time course of a volume flow through that one of the fluid guide units which is arranged downstream and a pressure in that one of the fluid guide units which is arranged downstream to follow a predefined time course, wherein the step of controlling at least one of the volume flow and the pressure comprises the step of setting at least one respective control pressure at the first valve and/or at the second valve; and wherein each valve of the valve device comprises a respective valve body and a valve body seat, wherein the valve body seat is configured such that a fluid can flow through the valve body seat, wherein the valve body is movable relative to the valve body seat, and wherein a cross-sectional area of the valve body seat of one valve of the valve device is smaller than a cross-sectional area of the valve body seat of another valve of the valve device.

\* \* \* \* \*